United States Patent
Lee et al.

(10) Patent No.: US 11,628,093 B2
(45) Date of Patent: *Apr. 18, 2023

(54) WOUND DRESSING

(71) Applicant: CONVATEC TECHNOLOGIES INC., Reno, NV (US)

(72) Inventors: Bryony Jayne Lee, Deeside (GB); Stephen Michael Cotton, Nottingham (GB)

(73) Assignee: ConvaTec Technologies, Inc., Las Vegas, NV (US)

( * ) Notice: Subject to any disclaimer, the term of this patent is extended or adjusted under 35 U.S.C. 154(b) by 124 days.

This patent is subject to a terminal disclaimer.

(21) Appl. No.: 16/893,178

(22) Filed: Jun. 4, 2020

(65) Prior Publication Data

US 2020/0306091 A1 Oct. 1, 2020

Related U.S. Application Data

(63) Continuation of application No. 12/437,647, filed on May 8, 2009, now Pat. No. 10,687,985.

(30) Foreign Application Priority Data

May 8, 2008 (GB) ..................................... 0808376

(51) Int. Cl.
*A61F 13/00* (2006.01)
*A61F 13/36* (2006.01)

(52) U.S. Cl.
CPC .. *A61F 13/00063* (2013.01); *A61F 13/00021* (2013.01); *A61F 13/00995* (2013.01);
(Continued)

(58) Field of Classification Search
CPC .. A61F 2013/00225; A61F 2013/00229; A61F 2013/00238; A61F 2013/00523; A61F 2013/0054; A61F 2013/00548; A61F 2013/00748; A61F 2013/00753; A61F 2013/00936; A61F 13/00063;
(Continued)

(56) References Cited

U.S. PATENT DOCUMENTS 3,521,632 A * 7/1970 Graham ................. A41D 13/12
602/41
5,807,295 A * 9/1998 Hutcheon ............. A61F 13/022
602/8
(Continued)

FOREIGN PATENT DOCUMENTS

EP 3187204 A1 7/2017
EP 3315145 A1 5/2018
(Continued)

OTHER PUBLICATIONS

Office Action Summary; Japanese Patent Office; Japanese Patent Application No. 2018-520573; dated Jul. 6, 2021; 8 pages.

*Primary Examiner* — Caitlin A Carreiro
(74) *Attorney, Agent, or Firm* — Taft Stettinius & Hollister LLP; Ryan O. White; Derek B. Lavender (57) ABSTRACT

A wound dressing including a layer in the form of a strip and including gel-forming fibers, the strip having longitudinal lines of stitches formed from a thread and transverse lines of stitches formed from a thread. In certain forms, the wound dressing includes at least one stitch free column.

18 Claims, 2 Drawing Sheets

(52) U.S. Cl.
CPC ...... *A61F 13/36* (2013.01); *A61F 2013/0054* (2013.01); *A61F 2013/00225* (2013.01); *A61F 2013/00229* (2013.01); *A61F 2013/00238* (2013.01); *A61F 2013/00523* (2013.01); *A61F 2013/00548* (2013.01); *A61F 2013/00714* (2013.01); *A61F 2013/00748* (2013.01); *A61F 2013/00753* (2013.01); *A61F 2013/00936* (2013.01)

(58) Field of Classification Search
CPC .......... A61F 13/00021; A61F 13/00995; A61F 13/36; A61F 13/00; A61F 13/00012; A61F 13/00029; B32B 23/00; B32B 23/02; B32B 23/04; A61L 15/00; A61L 15/16; A61L 15/44; A61L 15/60
USPC ........ 602/44, 45, 56, 76; 424/443, 445, 446, 424/447; 428/292.4
See application file for complete search history.

(56) References Cited

U.S. PATENT DOCUMENTS

| | | |
|---|---|---|
| 10,016,537 B2 | 7/2018 | Menon et al. |
| 10,046,096 B2 | 8/2018 | Askem et al. |
| 10,076,447 B2 | 9/2018 | Barta et al. |
| 10,076,587 B2 | 9/2018 | Locke et al. |
| 10,143,784 B2 | 12/2018 | Walton et al. |
| 10,426,670 B2 | 10/2019 | von Blucher et al. |
| 10,426,747 B2 | 10/2019 | Johnson |
| 10,426,874 B2 | 10/2019 | Chien et al. |
| 10,426,875 B2 | 10/2019 | Blott et al. |
| 10,426,938 B2 | 10/2019 | Locke et al. |
| 10,434,015 B2 | 10/2019 | Taylor et al. |
| 10,434,142 B2 | 10/2019 | Niazi et al. |
| 10,434,210 B2 | 10/2019 | Olson et al. |
| 10,434,284 B2 | 10/2019 | Hanson et al. |
| 10,449,094 B2 | 10/2019 | Donda et al. |
| D866,756 S | 11/2019 | Allen et al. |
| 10,463,760 B2 | 11/2019 | Karthikeyan et al. |
| 10,463,773 B2 | 11/2019 | Haggstrom et al. |
| 10,470,933 B2 | 11/2019 | Riesinger |
| 10,470,936 B2 | 11/2019 | Wohlgemuth et al. |
| 10,471,122 B2 | 11/2019 | Shi et al. |
| 10,471,190 B2 | 11/2019 | Locke et al. |
| 10,478,345 B2 | 11/2019 | Barta et al. |
| 10,478,346 B2 | 11/2019 | Knutson |
| 10,478,394 B2 | 11/2019 | Yu |
| 10,485,707 B2 | 11/2019 | Sexton |
| 10,485,891 B2 | 11/2019 | Andrews et al. |
| 10,485,892 B2 | 11/2019 | Hands et al. |
| 10,485,906 B2 | 11/2019 | Freedman et al. |
| 10,486,135 B2 | 11/2019 | Yang et al. |
| 10,492,956 B2 | 12/2019 | Zamierowski |
| 10,493,178 B2 | 12/2019 | Marchant et al. |
| 10,493,184 B2 | 12/2019 | Collinson et al. |
| 10,493,185 B2 | 12/2019 | Stokes et al. |
| 10,500,099 B2 | 12/2019 | Hung et al. |
| 10,500,103 B2 | 12/2019 | Croizat et al. |
| 10,500,104 B2 | 12/2019 | Sookraj |
| 10,500,173 B2 | 12/2019 | Yang et al. |
| 10,500,235 B2 | 12/2019 | Wardell |
| 10,500,300 B2 | 12/2019 | Dybe et al. |
| 10,500,301 B2 | 12/2019 | Laurensou |
| 10,500,302 B2 | 12/2019 | Holm et al. |
| 10,501,487 B2 | 12/2019 | Andrews et al. |
| 10,506,928 B2 | 12/2019 | Locke et al. |
| 10,507,141 B2 | 12/2019 | Allen et al. |
| 10,507,259 B2 | 12/2019 | Cree et al. |
| 10,512,707 B2 | 12/2019 | Whalen, III et al. |
| 10,525,170 B2 | 1/2020 | Havenstrite et al. |
| 10,532,137 B2 | 1/2020 | Pratt et al. |
| 10,532,194 B2 | 1/2020 | Locke et al. |
| 10,537,657 B2 | 1/2020 | Phillips et al. |
| 10,542,936 B2 | 1/2020 | Goldberg et al. |
| 10,543,133 B2 | 1/2020 | Shaw et al. |
| 10,543,293 B2 | 1/2020 | Suschek |
| 10,548,777 B2 | 2/2020 | Locke et al. |
| 10,549,008 B2 | 2/2020 | Yoo |
| 10,549,016 B2 | 2/2020 | Bushko et al. |
| 10,549,017 B2 | 2/2020 | Hsiao et al. |
| 10,555,838 B2 | 2/2020 | Wu et al. |
| 10,555,839 B2 | 2/2020 | Hartwell |
| 10,556,044 B2 | 2/2020 | Robinson et al. |
| 10,561,533 B2 | 2/2020 | Hoggarth et al. |
| 10,561,536 B2 | 2/2020 | Holm et al. |
| 10,568,767 B2 | 2/2020 | Addison et al. |
| 10,568,768 B2 | 2/2020 | Long et al. |
| 10,568,770 B2 | 2/2020 | Robinson et al. |
| 10,568,771 B2 | 2/2020 | MacDonald et al. |
| 10,568,773 B2 | 2/2020 | Tuck et al. |
| 10,568,983 B2 | 2/2020 | Gerdes et al. |
| 10,575,991 B2 | 3/2020 | Dunn |
| 10,575,992 B2 | 3/2020 | Sarangapani et al. |
| 10,576,037 B2 | 3/2020 | Harrell |
| 10,576,189 B2 | 3/2020 | Locke et al. |
| 10,583,042 B2 | 3/2020 | Sarangapani et al. |
| 10,583,228 B2 | 3/2020 | Shuler et al. |
| 10,589,007 B2 | 3/2020 | Coulthard et al. |
| 10,590,184 B2 | 3/2020 | Kuo |
| 10,610,414 B2 | 4/2020 | Hartwell et al. |
| 10,610,415 B2 | 4/2020 | Griffey et al. |
| 10,610,623 B2 | 4/2020 | Robinson et al. |
| 10,617,569 B2 | 4/2020 | Bonn |
| 10,617,608 B2 | 4/2020 | Shin et al. |
| 10,617,769 B2 | 4/2020 | Huang |
| 10,617,784 B2 | 4/2020 | Yu et al. |
| 10,617,786 B2 | 4/2020 | Kluge et al. |
| 10,618,266 B2 | 4/2020 | Wright et al. |
| 10,624,984 B2 | 4/2020 | Courage et al. |
| 10,625,002 B2 | 4/2020 | Locke et al. |
| 10,632,019 B2 | 4/2020 | Vitaris |
| 10,632,224 B2 | 4/2020 | Hardy et al. |
| 10,639,206 B2 | 5/2020 | Hu et al. |
| 10,639,350 B2 | 5/2020 | Arber et al. |
| 10,639,404 B2 | 5/2020 | Lichtenstein |
| 10,646,614 B2 | 5/2020 | Grinstaff et al. |
| 10,653,562 B2 | 5/2020 | Robinson et al. |
| 10,653,782 B2 | 5/2020 | Ameer et al. |
| 10,653,810 B2 | 5/2020 | Datt et al. |
| 10,653,821 B2 | 5/2020 | Nichols |
| 10,653,823 B2 | 5/2020 | Bharti et al. |
| 10,660,799 B2 | 5/2020 | Wu et al. |
| 10,660,851 B2 | 5/2020 | Millis et al. |
| 10,660,992 B2 | 5/2020 | Canner et al. |
| 10,660,994 B2 | 5/2020 | Askem et al. |
| 10,667,955 B2 | 6/2020 | Allen et al. |
| 10,667,956 B2 | 6/2020 | Van Holten et al. |
| 10,682,257 B2 | 6/2020 | Lu |
| 10,682,258 B2 | 6/2020 | Manwaring et al. |
| 10,682,259 B2 | 6/2020 | Hunt et al. |
| 10,682,318 B2 | 6/2020 | Twomey et al. |
| 10,682,386 B2 | 6/2020 | Ellis-Behnke et al. |
| 10,682,446 B2 | 6/2020 | Askem et al. |
| 10,687,983 B2 | 6/2020 | Dahlberg et al. |
| 10,687,985 B2 * | 6/2020 | Lee .................. A61F 13/36 |
| 10,688,215 B2 | 6/2020 | Munro et al. |
| 10,688,217 B2 | 6/2020 | Hanson et al. |
| RE48,117 E | 7/2020 | Albert et al. |
| 10,702,419 B2 | 7/2020 | Locke et al. |
| 10,702,420 B2 | 7/2020 | Hammond et al. |
| 10,703,942 B2 | 7/2020 | Tunius |
| 10,709,760 B2 | 7/2020 | Gronberg et al. |
| 10,709,807 B2 | 7/2020 | Kshirsagar |
| 10,709,883 B2 | 7/2020 | Spector |
| 10,716,711 B2 | 7/2020 | Locke et al. |
| 10,716,874 B2 | 7/2020 | Koyama et al. |
| 10,729,589 B2 | 8/2020 | Dorian et al. |
| 10,729,590 B2 | 8/2020 | Simmons et al. |
| 10,729,826 B2 | 8/2020 | Lin |
| 10,736,787 B2 | 8/2020 | Hannigan et al. |
| 10,736,788 B2 | 8/2020 | Locke et al. |
| 10,736,985 B2 | 8/2020 | Odermatt et al. |
| 10,737,003 B2 | 8/2020 | Fujisaki |

(56) References Cited

U.S. PATENT DOCUMENTS

| | | |
|---|---|---|
| 10,743,900 B2 | 8/2020 | Ingram et al. |
| 10,744,040 B2 | 8/2020 | Kazala, Jr. et al. |
| 10,744,041 B2 | 8/2020 | Hartwell |
| 10,744,225 B2 | 8/2020 | Lindgren et al. |
| 10,744,237 B2 | 8/2020 | Guidi et al. |
| 10,744,238 B2 | 8/2020 | Guidi et al. |
| 10,744,239 B2 | 8/2020 | Armstrong et al. |
| 10,744,240 B2 | 8/2020 | Simmons et al. |
| 10,751,212 B2 | 8/2020 | Raza et al. |
| 10,751,442 B2 | 8/2020 | Bonnefin et al. |
| 10,751,452 B2 | 8/2020 | Topaz |
| 10,758,423 B2 | 9/2020 | Pigg et al. |
| 10,758,424 B2 | 9/2020 | Biott et al. |
| 10,758,425 B2 | 9/2020 | Biott et al. |
| 10,758,426 B2 | 9/2020 | Eddy |
| 10,758,651 B2 | 9/2020 | Blott et al. |
| 10,765,561 B2 | 9/2020 | Lattimore et al. |
| 10,765,783 B2 | 9/2020 | Locke et al. |
| 10,772,767 B2 | 9/2020 | Bjork et al. |
| 10,772,999 B2 | 9/2020 | Svensby |
| 10,779,993 B2 | 9/2020 | Bishop et al. |
| 10,780,114 B2 | 9/2020 | Udagawa et al. |
| 10,780,194 B2 | 9/2020 | Flach et al. |
| 10,780,201 B2 | 9/2020 | Lin |
| 10,780,202 B2 | 9/2020 | Askem et al. |
| 10,780,203 B2 | 9/2020 | Coulthard et al. |
| 10,782,238 B2 | 9/2020 | Hicks et al. |
| 10,792,191 B2 | 10/2020 | Robinson et al. |
| 10,792,192 B2 | 10/2020 | Tout et al. |
| 10,792,337 B2 | 10/2020 | Leung et al. |
| 10,792,404 B2 | 10/2020 | Hu et al. |
| 10,792,482 B2 | 10/2020 | Randolph et al. |
| 10,800,905 B2 | 10/2020 | Delli-Santi et al. |
| 10,806,819 B2 | 10/2020 | Shuler |
| 11,076,997 B2 | 8/2021 | Hunt et al. |
| 11,191,866 B2 | 12/2021 | Bouvier et al. |
| 2006/0155260 A1 | 7/2006 | Blott et al. |
| 2006/0172000 A1 | 8/2006 | Cullen et al. |
| 2007/0042024 A1* | 2/2007 | Gladman ............ A61F 13/0273 424/445 |
| 2007/0185426 A1 | 8/2007 | Ambrosio et al. |
| 2007/0219512 A1 | 9/2007 | Heaton et al. |
| 2007/0239078 A1 | 10/2007 | Jaeb |
| 2009/0234307 A1 | 9/2009 | Vitaris |
| 2009/0259203 A1 | 10/2009 | Hu et al. |
| 2009/0293887 A1 | 12/2009 | Wilkes et al. |
| 2009/0299303 A1 | 12/2009 | Seegert |
| 2010/0015208 A1 | 1/2010 | Kershaw et al. |
| 2010/0030178 A1 | 2/2010 | MacMeccan et al. |
| 2010/0125233 A1 | 5/2010 | Edward S. et al. |
| 2010/0125258 A1 | 5/2010 | Coulthard et al. |
| 2010/0137775 A1 | 6/2010 | Hu et al. |
| 2010/0185163 A1 | 7/2010 | Heagle |
| 2010/0298790 A1 | 11/2010 | Guidi et al. |
| 2011/0015595 A1 | 1/2011 | Robinson et al. |
| 2011/0028918 A1 | 2/2011 | Hartwell |
| 2011/0112457 A1 | 5/2011 | Holm et al. |
| 2011/0178451 A1 | 7/2011 | Robinson et al. |
| 2011/0224593 A1 | 9/2011 | Tunius |
| 2011/0224630 A1 | 9/2011 | Simmons et al. |
| 2011/0230849 A1 | 9/2011 | Coulthard et al. |
| 2011/0251566 A1 | 10/2011 | Zimnitsky et al. |
| 2011/0257572 A1 | 10/2011 | Locke et al. |
| 2011/0257573 A1 | 10/2011 | Hong et al. |
| 2011/0275972 A1 | 11/2011 | Rosenberg |
| 2012/0071845 A1 | 3/2012 | Hu et al. |
| 2012/0130332 A1 | 5/2012 | Cotton et al. |
| 2012/0136325 A1 | 5/2012 | Allen et al. |
| 2012/0209226 A1 | 8/2012 | Simmons et al. |
| 2013/0053795 A1 | 2/2013 | Coulthard et al. |
| 2013/0123728 A1 | 5/2013 | Pratt et al. |
| 2013/0226063 A1 | 8/2013 | Taylor et al. |
| 2014/0005618 A1 | 1/2014 | Locke et al. |
| 2014/0074053 A1 | 3/2014 | Locke et al. |
| 2014/0188060 A1 | 7/2014 | Robinson et al. |
| 2014/0194838 A1 | 7/2014 | Wibaux et al. |
| 2014/0200532 A1 | 7/2014 | Robinson et al. |
| 2014/0236112 A1 | 8/2014 | Von Wolff et al. |
| 2014/0256925 A1 | 9/2014 | Catchmark et al. |
| 2014/0276499 A1 | 9/2014 | Locke et al. |
| 2014/0296804 A1 | 10/2014 | Hicks et al. |
| 2014/0308338 A1 | 10/2014 | Nierle et al. |
| 2014/0309574 A1 | 10/2014 | Cotton |
| 2015/0018433 A1 | 1/2015 | Leipzig et al. |
| 2015/0057624 A1 | 2/2015 | Simmons et al. |
| 2015/0071985 A1 | 3/2015 | Walker et al. |
| 2015/0079152 A1 | 3/2015 | Wuollett et al. |
| 2015/0094674 A1 | 4/2015 | Pratt et al. |
| 2015/0104486 A1 | 4/2015 | Bonnefin et al. |
| 2015/0112311 A1 | 4/2015 | Hammond et al. |
| 2015/0119831 A1 | 4/2015 | Robinson et al. |
| 2015/0119834 A1 | 4/2015 | Locke et al. |
| 2015/0141941 A1 | 5/2015 | Allen et al. |
| 2015/0148785 A1 | 5/2015 | Kleiner |
| 2015/0174304 A1 | 6/2015 | Askem et al. |
| 2015/0245949 A1 | 9/2015 | Locke et al. |
| 2015/0246164 A1 | 9/2015 | Heaton et al. |
| 2015/0250979 A1 | 9/2015 | Loske |
| 2015/0265741 A1 | 9/2015 | Duncan et al. |
| 2015/0265743 A1 | 9/2015 | Hanson et al. |
| 2015/0320901 A1 | 11/2015 | Chandrashekhar-Bhat et al. |
| 2016/0008293 A1 | 1/2016 | Shi et al. |
| 2016/0038626 A1 | 2/2016 | Locke et al. |
| 2016/0051724 A1 | 2/2016 | Sahin et al. |
| 2016/0067107 A1 | 3/2016 | Cotton |
| 2016/0100987 A1 | 4/2016 | Hartwell et al. |
| 2016/0106878 A1 | 4/2016 | Yang et al. |
| 2016/0106892 A1 | 4/2016 | Hartwell |
| 2016/0166422 A1 | 6/2016 | Karim et al. |
| 2016/0193244 A1 | 7/2016 | Ota et al. |
| 2016/0222548 A1 | 8/2016 | Agboh |
| 2016/0271178 A1 | 9/2016 | Hauser et al. |
| 2016/0287743 A1 | 10/2016 | Andrews |
| 2016/0339158 A1 | 11/2016 | Collinson et al. |
| 2016/0374847 A1 | 12/2016 | Lachenbruch et al. |
| 2017/0014275 A1 | 1/2017 | Schneider |
| 2017/0049111 A1 | 2/2017 | Patton et al. |
| 2017/0072669 A1 | 3/2017 | Sekido et al. |
| 2017/0128269 A1 | 5/2017 | Coulthard et al. |
| 2017/0189237 A1 | 7/2017 | Locke et al. |
| 2017/0189575 A1 | 7/2017 | Lee et al. |
| 2017/0209615 A1 | 7/2017 | Tornero Garcia et al. |
| 2017/0232161 A1 | 8/2017 | Fewkes et al. |
| 2017/0258956 A1 | 9/2017 | Flach et al. |
| 2017/0367895 A1 | 12/2017 | Holm et al. |
| 2017/0368239 A1 | 12/2017 | Askem et al. |
| 2018/0008742 A1 | 1/2018 | Hoggarth et al. |
| 2018/0014974 A1 | 1/2018 | Hoggarth et al. |
| 2018/0023217 A1 | 1/2018 | Patton et al. |
| 2018/0030321 A1 | 2/2018 | Tunius |
| 2018/0042789 A1 | 2/2018 | Bradford et al. |
| 2018/0078423 A1 | 3/2018 | Magin et al. |
| 2018/0086903 A1 | 3/2018 | Zhang et al. |
| 2018/0118809 A1 | 5/2018 | Mearns Spragg |
| 2018/0133066 A1 | 5/2018 | Ahsani et al. |
| 2018/0140467 A1 | 5/2018 | Hunt |
| 2018/0140822 A1 | 5/2018 | Robinson et al. |
| 2018/0200414 A1 | 7/2018 | Askem et al. |
| 2018/0221531 A1 | 8/2018 | Bender et al. |
| 2018/0236124 A1 | 8/2018 | Young et al. |
| 2018/0243463 A1 | 8/2018 | Chatterjee et al. |
| 2018/0243464 A1 | 8/2018 | Hwang et al. |
| 2018/0244857 A1 | 8/2018 | Lee et al. |
| 2018/0272052 A1 | 9/2018 | Locke et al. |
| 2018/0296397 A1 | 10/2018 | Askem et al. |
| 2018/0303873 A1 | 10/2018 | Been et al. |
| 2018/0311419 A1 | 11/2018 | Locke et al. |
| 2018/0333522 A1 | 11/2018 | Pratt et al. |
| 2018/0344533 A1 | 12/2018 | Rovaniemi |
| 2018/0353334 A1 | 12/2018 | Locke et al. |
| 2018/0353337 A1 | 12/2018 | Locke |
| 2018/0353339 A1 | 12/2018 | Locke et al. |
| 2018/0353340 A1 | 12/2018 | Robinson et al. |
| 2018/0353344 A1 | 12/2018 | Locke et al. |

(56) References Cited

U.S. PATENT DOCUMENTS

| | | |
|---|---|---|
| 2018/0353662 A1 | 12/2018 | Locke et al. |
| 2018/0353663 A1 | 12/2018 | Locke et al. |
| 2018/0360667 A1 | 12/2018 | Droche |
| 2019/0000677 A1 | 1/2019 | Munro |
| 2019/0015258 A1 | 1/2019 | Gowans et al. |
| 2019/0015468 A1 | 1/2019 | Yadav et al. |
| 2019/0030223 A1 | 1/2019 | Lin |
| 2019/0046682 A1 | 2/2019 | Choi et al. |
| 2019/0060127 A1 | 2/2019 | Locke et al. |
| 2019/0083752 A1 | 3/2019 | Howell et al. |
| 2019/0117465 A1 | 4/2019 | Osborne et al. |
| 2019/0117466 A1 | 4/2019 | Kazala, Jr. et al. |
| 2019/0117861 A1 | 4/2019 | Locke et al. |
| 2019/0125590 A1 | 5/2019 | Rehbein et al. |
| 2019/0133830 A1 | 5/2019 | Bishop et al. |
| 2019/0151155 A1 | 5/2019 | Bonn |
| 2019/0151159 A1 | 5/2019 | Gowans et al. |
| 2019/0151495 A1 | 5/2019 | Helary et al. |
| 2019/0184052 A1 | 6/2019 | Ilan et al. |
| 2019/0231600 A1 | 8/2019 | Locke et al. |
| 2019/0231602 A1 | 8/2019 | Locke et al. |
| 2019/0231943 A1 | 8/2019 | Robinson et al. |
| 2019/0274889 A1 | 9/2019 | Steward et al. |
| 2019/0282728 A1 | 9/2019 | Kellar et al. |
| 2019/0290799 A1 | 9/2019 | Arshi et al. |
| 2019/0298249 A1 | 10/2019 | Bates et al. |
| 2019/0298577 A1 | 10/2019 | Locke et al. |
| 2019/0298578 A1 | 10/2019 | Shulman et al. |
| 2019/0298579 A1 | 10/2019 | Moore et al. |
| 2019/0298580 A1 | 10/2019 | Hall et al. |
| 2019/0298582 A1 | 10/2019 | Addison et al. |
| 2019/0298881 A1 | 10/2019 | Ramjit et al. |
| 2019/0298882 A1 | 10/2019 | Nelson |
| 2019/0298895 A1 | 10/2019 | Selby et al. |
| 2019/0307611 A1 | 10/2019 | Askem et al. |
| 2019/0307612 A1 | 10/2019 | Hartwell et al. |
| 2019/0307934 A1 | 10/2019 | Allen et al. |
| 2019/0307935 A1 | 10/2019 | Simmons et al. |
| 2019/0314187 A1 | 10/2019 | Emslander et al. |
| 2019/0314209 A1 | 10/2019 | Ha et al. |
| 2019/0314544 A1 | 10/2019 | Filho et al. |
| 2019/0321232 A1 | 10/2019 | Jardret et al. |
| 2019/0321509 A1 | 10/2019 | Chakravarthy et al. |
| 2019/0321526 A1 | 10/2019 | Robinson et al. |
| 2019/0322795 A1 | 10/2019 | Kubo et al. |
| 2019/0328580 A1 | 10/2019 | Emslander et al. |
| 2019/0336343 A1 | 11/2019 | Etchells et al. |
| 2019/0336344 A1 | 11/2019 | Locke |
| 2019/0336345 A1 | 11/2019 | Bannwart |
| 2019/0336346 A1 | 11/2019 | Locke et al. |
| 2019/0336640 A1 | 11/2019 | Vismara et al. |
| 2019/0336641 A1 | 11/2019 | Nisbet |
| 2019/0336643 A1 | 11/2019 | Luukko et al. |
| 2019/0336658 A1 | 11/2019 | Heaton et al. |
| 2019/0336739 A1 | 11/2019 | Locke et al. |
| 2019/0343687 A1 | 11/2019 | Locke et al. |
| 2019/0343889 A1 | 11/2019 | Luukko et al. |
| 2019/0343979 A1 | 11/2019 | Kearney et al. |
| 2019/0343993 A1 | 11/2019 | Weston |
| 2019/0343994 A1 | 11/2019 | Greener |
| 2019/0344242 A1 | 11/2019 | Kim et al. |
| 2019/0350763 A1 | 11/2019 | Pratt et al. |
| 2019/0350764 A1 | 11/2019 | Zochowski et al. |
| 2019/0350765 A1 | 11/2019 | Heagle et al. |
| 2019/0350775 A1 | 11/2019 | Biasutti et al. |
| 2019/0350970 A1 | 11/2019 | Saphier et al. |
| 2019/0351092 A1 | 11/2019 | Silver et al. |
| 2019/0351093 A1 | 11/2019 | Stein et al. |
| 2019/0351094 A1 | 11/2019 | Maher et al. |
| 2019/0351095 A1 | 11/2019 | Maher et al. |
| 2019/0351111 A1 | 11/2019 | Locke et al. |
| 2019/0358088 A1 | 11/2019 | Lavocah et al. |
| 2019/0358361 A1 | 11/2019 | McInnes et al. |
| 2019/0358372 A1 | 11/2019 | Askem et al. |
| 2019/0365948 A1 | 12/2019 | Deegan et al. |
| 2019/0365962 A1 | 12/2019 | Lee et al. |
| 2019/0374408 A1 | 12/2019 | Robles et al. |
| 2019/0374673 A1 | 12/2019 | Hoefinghoff et al. |
| 2019/0380878 A1 | 12/2019 | Edwards et al. |
| 2019/0380881 A1 | 12/2019 | Albert et al. |
| 2019/0380882 A1 | 12/2019 | Taylor et al. |
| 2019/0380883 A1 | 12/2019 | MacPhee et al. |
| 2019/0381222 A9 | 12/2019 | Locke et al. |
| 2019/0388577 A1 | 12/2019 | Chandrashekhar-Bhat et al. |
| 2019/0388579 A1 | 12/2019 | MacPhee et al. |
| 2019/0388589 A1 | 12/2019 | MacPhee et al. |
| 2020/0000640 A1 | 1/2020 | Mondal et al. |
| 2020/0000642 A1 | 1/2020 | Waite |
| 2020/0000643 A1 | 1/2020 | Locke |
| 2020/0000955 A1 | 1/2020 | Andrews et al. |
| 2020/0000956 A1 | 1/2020 | Huang et al. |
| 2020/0000960 A1 | 1/2020 | Kellar et al. |
| 2020/0000985 A1 | 1/2020 | Seddon et al. |
| 2020/0008981 A1 | 1/2020 | Wheldrake |
| 2020/0009289 A1 | 1/2020 | Torabinejad et al. |
| 2020/0009400 A1 | 1/2020 | Ribeiro et al. |
| 2020/0017650 A1 | 1/2020 | Young et al. |
| 2020/0022844 A1 | 1/2020 | Blott et al. |
| 2020/0023102 A1 | 1/2020 | Powell |
| 2020/0023103 A1 | 1/2020 | Joshi et al. |
| 2020/0023104 A1 | 1/2020 | Eriksson et al. |
| 2020/0023105 A1 | 1/2020 | Long et al. |
| 2020/0023106 A1 | 1/2020 | Carroll et al. |
| 2020/0030153 A1 | 1/2020 | Johannison et al. |
| 2020/0030480 A1 | 1/2020 | Choi |
| 2020/0030499 A1 | 1/2020 | Menon et al. |
| 2020/0038023 A1 | 2/2020 | Dunn |
| 2020/0038249 A1 | 2/2020 | Pratt et al. |
| 2020/0038250 A1 | 2/2020 | Edwards et al. |
| 2020/0038251 A1 | 2/2020 | Locke et al. |
| 2020/0038252 A1 | 2/2020 | Spiro |
| 2020/0038283 A1 | 2/2020 | Hall et al. |
| 2020/0038470 A1 | 2/2020 | Datt et al. |
| 2020/0038544 A1 | 2/2020 | Grover et al. |
| 2020/0038546 A1 | 2/2020 | Dizio et al. |
| 2020/0038639 A1 | 2/2020 | Patel et al. |
| 2020/0046565 A1 | 2/2020 | Barta et al. |
| 2020/0046566 A1 | 2/2020 | Carey et al. |
| 2020/0046567 A1 | 2/2020 | Carroll et al. |
| 2020/0046568 A1 | 2/2020 | Sexton |
| 2020/0046663 A1 | 2/2020 | Murdock et al. |
| 2020/0046876 A1 | 2/2020 | Liu |
| 2020/0046887 A1 | 2/2020 | Runquist et al. |
| 2020/0054491 A1 | 2/2020 | Hentrich et al. |
| 2020/0054781 A1 | 2/2020 | Weiser et al. |
| 2020/0060879 A1 | 2/2020 | Edwards et al. |
| 2020/0061253 A1 | 2/2020 | Long et al. |
| 2020/0061254 A1 | 2/2020 | Joshi et al. |
| 2020/0061379 A1 | 2/2020 | Bogie et al. |
| 2020/0069183 A1 | 3/2020 | Rice et al. |
| 2020/0069476 A1 | 3/2020 | Randolph et al. |
| 2020/0069477 A1 | 3/2020 | Holm et al. |
| 2020/0069478 A1 | 3/2020 | Jabbarzadeh et al. |
| 2020/0069479 A1 | 3/2020 | Buan et al. |
| 2020/0069835 A1 | 3/2020 | Hissink et al. |
| 2020/0069850 A1 | 3/2020 | Beadle et al. |
| 2020/0069851 A1 | 3/2020 | Blott et al. |
| 2020/0069853 A1 | 3/2020 | Hall et al. |
| 2020/0078223 A1 | 3/2020 | Locke et al. |
| 2020/0078224 A1 | 3/2020 | Carroll et al. |
| 2020/0078225 A1 | 3/2020 | Grillitsch et al. |
| 2020/0078305 A1 | 3/2020 | Auvinen et al. |
| 2020/0078330 A1 | 3/2020 | Gay |
| 2020/0078482 A1 | 3/2020 | Yoon et al. |
| 2020/0078499 A1 | 3/2020 | Gadde et al. |
| 2020/0085625 A1 | 3/2020 | Bellini et al. |
| 2020/0085626 A1 | 3/2020 | Braga et al. |
| 2020/0085629 A1 | 3/2020 | Locke et al. |
| 2020/0085630 A1 | 3/2020 | Robinson et al. |
| 2020/0085632 A1 | 3/2020 | Locke et al. |
| 2020/0085991 A1 | 3/2020 | Coomber |
| 2020/0085992 A1 | 3/2020 | Locke et al. |
| 2020/0086014 A1 | 3/2020 | Locke et al. |
| 2020/0086017 A1 | 3/2020 | Jardret et al. |

(56) References Cited

U.S. PATENT DOCUMENTS

| | | |
|---|---|---|
| 2020/0086049 A1 | 3/2020 | Park et al. |
| 2020/0093646 A1 | 3/2020 | Locke et al. |
| 2020/0093756 A1 | 3/2020 | Sabacinski |
| 2020/0093953 A1 | 3/2020 | Kim et al. |
| 2020/0093954 A1 | 3/2020 | Leise, III |
| 2020/0093970 A1 | 3/2020 | Hunt et al. |
| 2020/0095421 A1 | 3/2020 | Kettel |
| 2020/0100945 A1 | 4/2020 | Albert et al. |
| 2020/0101192 A1 | 4/2020 | Folwarzny |
| 2020/0107964 A1 | 4/2020 | Locke et al. |
| 2020/0107965 A1 | 4/2020 | Greener |
| 2020/0107966 A1 | 4/2020 | Francis |
| 2020/0107967 A1 | 4/2020 | Holm et al. |
| 2020/0108169 A1 | 4/2020 | Hu et al. |
| 2020/0113741 A1 | 4/2020 | Rehbein et al. |
| 2020/0114039 A1 | 4/2020 | Wang et al. |
| 2020/0114040 A1 | 4/2020 | Waite et al. |
| 2020/0114049 A1 | 4/2020 | Wall |
| 2020/0121509 A1 | 4/2020 | Locke et al. |
| 2020/0121510 A1 | 4/2020 | Hartwell et al. |
| 2020/0121513 A1 | 4/2020 | Townsend et al. |
| 2020/0121521 A1 | 4/2020 | Daniel et al. |
| 2020/0121833 A9 | 4/2020 | Askem et al. |
| 2020/0129338 A1 | 4/2020 | Gardiner et al. |
| 2020/0129341 A1 | 4/2020 | Coulthard et al. |
| 2020/0129648 A1 | 4/2020 | Drury et al. |
| 2020/0129654 A1 | 4/2020 | Bouvier et al. |
| 2020/0129655 A1 | 4/2020 | Gardiner et al. |
| 2020/0129675 A1 | 4/2020 | Robinson et al. |
| 2020/0138754 A1 | 5/2020 | Johnson |
| 2020/0139002 A1 | 5/2020 | Dudnyk et al. |
| 2020/0139023 A1 | 5/2020 | Haggstrom et al. |
| 2020/0139025 A1 | 5/2020 | Robinson et al. |
| 2020/0141031 A1 | 5/2020 | Kosan et al. |
| 2020/0146894 A1 | 5/2020 | Long et al. |
| 2020/0146896 A1 | 5/2020 | Rice et al. |
| 2020/0146897 A1 | 5/2020 | Locke et al. |
| 2020/0146899 A1 | 5/2020 | Pratt et al. |
| 2020/0155355 A1 | 5/2020 | Hill et al. |
| 2020/0155358 A1 | 5/2020 | Wheldrake |
| 2020/0155359 A1 | 5/2020 | Carroll et al. |
| 2020/0155361 A1 | 5/2020 | Pigg et al. |
| 2020/0155379 A1 | 5/2020 | Shaw et al. |
| 2020/0163802 A1 | 5/2020 | Hunt et al. |
| 2020/0163803 A1 | 5/2020 | Pigg et al. |
| 2020/0164112 A1 | 5/2020 | Kato et al. |
| 2020/0164120 A1 | 5/2020 | Jaecklein et al. |
| 2020/0170841 A1 | 6/2020 | Waite et al. |
| 2020/0170842 A1 | 6/2020 | Locke |
| 2020/0170843 A1 | 6/2020 | Collinson et al. |
| 2020/0171197 A1 | 6/2020 | Hubbell et al. |
| 2020/0179300 A1 | 6/2020 | Urban et al. |
| 2020/0179558 A1 | 6/2020 | Munro et al. |
| 2020/0179673 A1 | 6/2020 | Wan |
| 2020/0188179 A1 | 6/2020 | Bugedo-Albizuri et al. |
| 2020/0188180 A1 | 6/2020 | Akbari et al. |
| 2020/0188182 A1 | 6/2020 | Sanders et al. |
| 2020/0188183 A1 | 6/2020 | Hamerslagh et al. |
| 2020/0188550 A1 | 6/2020 | Dagger et al. |
| 2020/0188564 A1 | 6/2020 | Dunn |
| 2020/0190310 A1 | 6/2020 | Meyer |
| 2020/0197227 A1 | 6/2020 | Locke et al. |
| 2020/0197228 A1 | 6/2020 | Hartwell |
| 2020/0197559 A1 | 6/2020 | Bourdillon et al. |
| 2020/0197580 A1 | 6/2020 | Kilpadi et al. |
| 2020/0206035 A1 | 7/2020 | Kantor et al. |
| 2020/0206036 A1 | 7/2020 | Robinson et al. |
| 2020/0214637 A1 | 7/2020 | Brownhill et al. |
| 2020/0214897 A1 | 7/2020 | Long et al. |
| 2020/0214898 A1 | 7/2020 | Waite et al. |
| 2020/0214899 A1 | 7/2020 | Locke et al. |
| 2020/0215220 A1 | 7/2020 | Schomburg et al. |
| 2020/0215226 A1 | 7/2020 | Kitagawa et al. |
| 2020/0222469 A1 | 7/2020 | Cotton |
| 2020/0229983 A1 | 7/2020 | Robinson et al. |
| 2020/0230283 A1 | 7/2020 | Yang et al. |
| 2020/0237562 A1 | 7/2020 | Rice et al. |
| 2020/0237564 A1 | 7/2020 | Hammond et al. |
| 2020/0237816 A1 | 7/2020 | Lait |
| 2020/0246190 A1 | 8/2020 | Luckemeyer et al. |
| 2020/0246191 A1 | 8/2020 | Lu et al. |
| 2020/0246194 A1 | 8/2020 | Gonzalez et al. |
| 2020/0246195 A1 | 8/2020 | Robinson et al. |
| 2020/0253785 A1 | 8/2020 | Bernet et al. |
| 2020/0253786 A1 | 8/2020 | Harrison et al. |
| 2020/0253788 A1 | 8/2020 | Rehbein et al. |
| 2020/0254139 A1 | 8/2020 | Phillips et al. |
| 2020/0261275 A1 | 8/2020 | Manwaring et al. |
| 2020/0261276 A1 | 8/2020 | Lujan Hernandez et al. |
| 2020/0268560 A1 | 8/2020 | Harrison et al. |
| 2020/0268561 A1 | 8/2020 | Locke et al. |
| 2020/0269028 A1 | 8/2020 | Hegg |
| 2020/0270484 A1 | 8/2020 | Lipscomb et al. |
| 2020/0276055 A1 | 9/2020 | Randolph et al. |
| 2020/0276058 A1 | 9/2020 | Locke et al. |
| 2020/0277450 A1 | 9/2020 | Silverstein et al. |
| 2020/0281519 A1 | 9/2020 | Gowans et al. |
| 2020/0281529 A1 | 9/2020 | Grubb et al. |
| 2020/0281678 A1 | 9/2020 | Long et al. |
| 2020/0281775 A1 | 9/2020 | Kushnir et al. |
| 2020/0282100 A1 | 9/2020 | Gil et al. |
| 2020/0282114 A1 | 9/2020 | Long et al. |
| 2020/0282115 A1 | 9/2020 | Gardner et al. |
| 2020/0289326 A1 | 9/2020 | Nielsen et al. |
| 2020/0289327 A1 | 9/2020 | Hansen et al. |
| 2020/0289328 A1 | 9/2020 | Luckemeyer et al. |
| 2020/0289346 A1 | 9/2020 | Hansen et al. |
| 2020/0289347 A1 | 9/2020 | Gowans et al. |
| 2020/0289701 A1 | 9/2020 | Hall et al. |
| 2020/0289712 A1 | 9/2020 | Jiang et al. |
| 2020/0289723 A1 | 9/2020 | Gregory et al. |
| 2020/0289726 A1 | 9/2020 | Locke et al. |
| 2020/0289727 A1 | 9/2020 | Locke |
| 2020/0289806 A1 | 9/2020 | Locke et al. |
| 2020/0297541 A1 | 9/2020 | Hartwell et al. |
| 2020/0297543 A1 | 9/2020 | Rodzewicz et al. |
| 2020/0297544 A1 | 9/2020 | Moine et al. |
| 2020/0297892 A1 | 9/2020 | Silcock |
| 2020/0297893 A1 | 9/2020 | Ericson |
| 2020/0297894 A1 | 9/2020 | Koyama et al. |
| 2020/0299865 A1 | 9/2020 | Bonnefin et al. |
| 2020/0306089 A1 | 10/2020 | Delury et al. |
| 2020/0306091 A1 | 10/2020 | Lee et al. |
| 2020/0306092 A1 | 10/2020 | Rehbein et al. |
| 2020/0306094 A1 | 10/2020 | Kushnir et al. |
| 2020/0306426 A1 | 10/2020 | Rice et al. |
| 2020/0306428 A1 | 10/2020 | Ingram et al. |
| 2020/0306430 A1 | 10/2020 | Rehbein et al. |
| 2020/0315853 A1 | 10/2020 | Waite |
| 2020/0315854 A1 | 10/2020 | Simmons et al. |
| 2020/0315894 A1 | 10/2020 | Churilla et al. |
| 2020/0316271 A1 | 10/2020 | Lin |
| 2020/0316272 A1 | 10/2020 | Simpson |
| 2020/0316273 A1 | 10/2020 | Hegg |
| 2020/0323692 A1 | 10/2020 | Locke et al. |
| 2020/0324015 A1 | 10/2020 | Kettel et al. |
| 2020/0330283 A1 | 10/2020 | Locke et al. |
| 2020/0330284 A1 | 10/2020 | Locke et al. |
| 2020/0330285 A1 | 10/2020 | Rehbein et al. |
| 2020/0330658 A1 | 10/2020 | Fujisaki |
| 2020/0330660 A1 | 10/2020 | Patel et al. |
| 2020/0337719 A1 | 10/2020 | Ingram et al. |
| 2020/0337904 A1 | 10/2020 | Waite |
| 2020/0337905 A1 | 10/2020 | Earl et al. |
| 2020/0337906 A1 | 10/2020 | Long et al. |
| 2020/0337908 A1 | 10/2020 | Long et al. |
| 2020/0338228 A1 | 10/2020 | Kharkar et al. |
| 2020/0338243 A1 | 10/2020 | Harrison et al. |
| 2021/0177662 A1 | 6/2021 | Locke et al. |
| 2021/0275693 A1 | 9/2021 | Ballamy |
| 2021/0338486 A1 | 11/2021 | Dagger et al. |
| 2021/0378876 A1 | 12/2021 | Gowans |
| 2021/0393443 A1 | 12/2021 | Steven et al. |

(56) References Cited

U.S. PATENT DOCUMENTS

2022/0001212 A1 1/2022 Bass et al.
2022/0031231 A1 2/2022 Hunt et al.
2022/0142822 A1 5/2022 Cotton

FOREIGN PATENT DOCUMENTS

| | | |
|---|---|---|
| EP | 3556407 A1 | 10/2019 |
| EP | 3569260 A1 | 11/2019 |
| EP | 3622975 A1 | 3/2020 |
| EP | 3643328 A1 | 4/2020 |
| EP | 3643330 A1 | 4/2020 |
| EP | 3643331 A1 | 4/2020 |
| EP | 3669838 A1 | 6/2020 |
| EP | 3669843 A1 | 6/2020 |
| EP | 3669844 A1 | 6/2020 |
| EP | 3838238 A1 | 6/2021 |
| EP | 3846757 | 7/2021 |
| EP | 3866920 | 8/2021 |
| EP | 3681452 B1 | 12/2021 |
| EP | 3454807 B1 | 4/2022 |
| GB | 2579211 A | 6/2020 |
| GB | 2579368 A | 6/2020 |
| GB | 2592804 A | 9/2021 |
| GB | 2592805 A | 9/2021 |
| GB | 2592806 A | 9/2021 |
| JP | 2002210020 A | 7/2002 |
| WO | 2005018543 A2 | 3/2005 |
| WO | 2011121394 A1 | 10/2011 |
| WO | 2011135284 A1 | 11/2011 |
| WO | 2011144888 A1 | 11/2011 |
| WO | 2013015827 A2 | 1/2013 |
| WO | 2013126049 A1 | 8/2013 |
| WO | 2014014842 A1 | 1/2014 |
| WO | 2015145117 A1 | 10/2015 |
| WO | 2015173546 A1 | 11/2015 |
| WO | 2016141450 A1 | 9/2016 |
| WO | 2017016974 A1 | 2/2017 |
| WO | 2017125250 A1 | 7/2017 |
| WO | 2018029231 A1 | 2/2018 |
| WO | 2018094061 A1 | 5/2018 |
| WO | 2018162613 A1 | 9/2018 |
| WO | 2018163093 A1 | 9/2018 |
| WO | 2018189265 A1 | 10/2018 |
| WO | 2018226667 A1 | 12/2018 |
| WO | 2018227144 A1 | 12/2018 |
| WO | 2018231825 A1 | 12/2018 |
| WO | 2018236648 A1 | 12/2018 |
| WO | 2019002085 A1 | 1/2019 |
| WO | 2019012068 A1 | 1/2019 |
| WO | 2019012069 A1 | 1/2019 |
| WO | 2019022493 A1 | 1/2019 |
| WO | 2019027933 A1 | 2/2019 |
| WO | 2019038548 A1 | 2/2019 |
| WO | 2019038549 A1 | 2/2019 |
| WO | 2019040656 A1 | 2/2019 |
| WO | 2019050855 A1 | 3/2019 |
| WO | 2019058373 A1 | 3/2019 |
| WO | 2019073326 A1 | 4/2019 |
| WO | 2019083563 A1 | 5/2019 |
| WO | 2019083868 A1 | 5/2019 |
| WO | 2019086911 A1 | 5/2019 |
| WO | 2019091150 A1 | 5/2019 |
| WO | 2019094147 A1 | 5/2019 |
| WO | 2019096828 A1 | 5/2019 |
| WO | 2019113275 A1 | 6/2019 |
| WO | 2019113623 A1 | 6/2019 |
| WO | 2019191590 A1 | 10/2019 |
| WO | 2019193141 A1 | 10/2019 |
| WO | 2019193333 A1 | 10/2019 |
| WO | 2019199389 A1 | 10/2019 |
| WO | 2019199596 A1 | 10/2019 |
| WO | 2019199687 A1 | 10/2019 |
| WO | 2019199798 A1 | 10/2019 |
| WO | 2019199849 A1 | 10/2019 |
| WO | 2019200035 A1 | 10/2019 |
| WO | 2019215572 A1 | 11/2019 |
| WO | 2019219613 A1 | 11/2019 |
| WO | 2019234365 A1 | 12/2019 |
| WO | 2020005344 A1 | 1/2020 |
| WO | 2020005536 A1 | 1/2020 |
| WO | 2020005546 A1 | 1/2020 |
| WO | 2020005577 A1 | 1/2020 |
| WO | 2020007429 A1 | 1/2020 |
| WO | 2020011691 A1 | 1/2020 |
| WO | 2020014178 A1 | 1/2020 |
| WO | 2020014310 A1 | 1/2020 |
| WO | 2020018300 A1 | 1/2020 |
| WO | 2020095062 A1 | 1/2020 |
| WO | 2020026061 A1 | 2/2020 |
| WO | 2020026144 A1 | 2/2020 |
| WO | 2020033351 A1 | 2/2020 |
| WO | 2020035811 A1 | 2/2020 |
| WO | 2020043665 A1 | 3/2020 |
| WO | 2020044237 A1 | 3/2020 |
| WO | 2020046443 A1 | 3/2020 |
| WO | 2020047255 A1 | 3/2020 |
| WO | 2020049038 A1 | 3/2020 |
| WO | 2020055945 A1 | 3/2020 |
| WO | 2020056014 A1 | 3/2020 |
| WO | 2020056182 A1 | 3/2020 |
| WO | 2020065531 A1 | 4/2020 |
| WO | 2020070231 A1 | 4/2020 |
| WO | 2020074512 A1 | 4/2020 |
| WO | 2020078993 A1 | 4/2020 |
| WO | 2020079009 A1 | 4/2020 |
| WO | 2020079330 A1 | 4/2020 |
| WO | 2020081259 A1 | 4/2020 |
| WO | 2020081391 A1 | 4/2020 |
| WO | 2020092598 A1 | 5/2020 |
| WO | 2020136555 A1 | 7/2020 |
| WO | 2020141059 A1 | 7/2020 |
| WO | 2020144347 A1 | 7/2020 |
| WO | 2020150548 A1 | 7/2020 |
| WO | 2020159675 A1 | 8/2020 |
| WO | 2020159677 A1 | 8/2020 |
| WO | 2020159678 A1 | 8/2020 |
| WO | 2020159823 A1 | 8/2020 |
| WO | 2020159859 A1 | 8/2020 |
| WO | 2020159892 A1 | 8/2020 |
| WO | 2020161086 A1 | 8/2020 |
| WO | 2020173665 A1 | 9/2020 |
| WO | 2020173760 A1 | 9/2020 |
| WO | 2020174264 A1 | 9/2020 |
| WO | 2020174510 A1 | 9/2020 |
| WO | 2020182887 A1 | 9/2020 |
| WO | 2020185810 A1 | 9/2020 |
| WO | 2020197759 A1 | 10/2020 |
| WO | 2020197760 A1 | 10/2020 |
| WO | 2020198484 A1 | 10/2020 |
| WO | 2020201879 A1 | 10/2020 |
| WO | 2020213998 A1 | 10/2020 |

* cited by examiner

WOUND DRESSING

This invention relates to a wound dressing, in particular, to ribbon or strip dressing of the type composed of gel-forming fibers in the form of a woven or nonwoven layer or layers. In particular, the invention relates to dressings comprising gel-forming fibers used in the treatment of sinus or cavity wounds or post-operative wounds.

BACKGROUND OF THE INVENTION

It is known to use carboxymethylated cellulosic materials in situations where a high degree of exudate absorption is required. For example, WO 93/12275 describes the production of various absorbent products capable of absorbing many times their own weight of water. This causes the carboxymethylated fibers to form a gel. WO 94/16746 and WO 00/01425 describe the use of carboxymethylated Lyocell materials in wound dressings where the advantages of gel formation in preventing adherence and, therefore, reducing wound damage and pain on removal are discussed.

Known wound dressings comprising gel-forming fibers are essentially flat, rectangular and fairly small, typically 20 cm×15 cm. The usefulness of such dressings is limited with respect to sinus or cavity wounds due to difficulty in removing the dressing from such a wound. The gel-forming fibers gel on absorption of exudate and consequently lose tensile strength once in a gelled state. This presents a problem when the dressing needs to be removed as removal generally is done by pulling the ribbon out of the wound from one end of the ribbon. The loss of tensile strength means that the dressing fragments on removal and has to be removed in many pieces or by flushing.

However, it would be desirable to bring the advantages of gel-forming fiber dressings to cavity wounds by having the dressings available in a strip form with sufficient tensile strength to enable the dressing to be removed in one piece from the wound once it has gelled and to be removed in one piece regardless of which part of the dressing is grasped in the removal.

It is known to form ribbon dressings with a reinforcing scrim in order to improve the tensile strength of the dressing. There are, however, disadvantages in doing so. The scrim detracts from the absorbency of the dressing and can create a physical barrier to absorption. The scrim also renders the dressing opaque which means that the wound and surrounding skin cannot be observed once the dressing is in situ.

It is known to increase the tensile strength of bandages by stitching the bandage along its length with one or more lines of stitching. However, when longitudinal stitching is applied to a thin strip it gives strength only in the stitching direction and restricts how the dressing can be removed.

SUMMARY OF THE INVENTION

The present invention seeks to provide improved wound dressings which mitigate the problems associated with ribbon dressings in cavity or sinus wounds.

We have now found that it is possible to improve the tensile strength of strip dressings in a dry or wet (gelled) state.

Accordingly, the invention provides a wound dressing comprising a layer in the form of a strip and comprising gel-forming fibers, the strip having longitudinal lines of stitches formed from a thread and transverse lines of stitches formed from a thread.

The longitudinal stitching is longitudinal in that it is generally parallel to the long dimension of the strip.

The transverse stitching is transverse in that it joins the longitudinal lines of stitches together and in some embodiments is generally perpendicular to the long dimension of the strip.

The thread may be a single filament or multiple filament yarn or a staple fiber yarn. The thread can be cellulosic, lycra, nylon, polyester or polyurethane. The thread can be impregnated with an active agent, for example, with an antimicrobial agent.

Such dressings are suited to treating sinus or cavity wounds, post operative or surgical wounds or any wound that needs to be packed. Additionally, such dressings can be used as part of a composite dressing if desired.

The longitudinal stitching preferably passes through the whole thickness of the strip and can be visible on both sides of the strip. The transverse stitching may also pass through the whole thickness of the strip or may be present on one side only of the strip or both.

By gel-forming fibers is meant hygroscopic fibers which upon the uptake of wound exudate become moist slippery or gelatinous and thus reduce the tendency for the surrounding fibers to adhere to the wound. The gel-forming fibers can be of the type which retain their structural integrity on absorption of exudate or can be of the type which lose their fibrous form and become a structureless gel. The gel-forming fibers are, preferably, spun sodium carboxymethylcellulose fibers, chemically modified cellulosic fibers, pectin fibers, alginate fibers, chitosan fibers, hyaluronic acid fibers, or other polysaccharide fibers or fibers derived from gums. The cellulosic fibers, preferably, have a degree of substitution of at least 0.05 carboxymethyl groups per glucose unit. The gel-forming fibers, preferably, have an absorbency of at least 2 grams 0.9% saline solution per gram of fiber (as measured by the free swell method).

Preferably, the gel-forming fibers have an absorbency of at least 10 g/g as measured in the free well absorbency method, more preferably between 15 g/g and 25 g/g.

The dressing may, for instance, comprise non gel-forming fibers and, in particular, may comprise lycra or other elastic fibre.

The dressing may be in the form of 0.5, 1, 2 or more meter lengths and be approximately 0.5 cm to 10 cm wide, preferably from 0.5 cm to 5 cm wide. The longitudinal lines of stitching may be from 1 mm to 10 mm apart and, preferably, from 2 mm to 5 mm apart. The lines of longitudinal stitching may be a lock stitch and may typically be crochet or chain stitch, but other stitch patterns may also be used. The rows of transverse stitching may be from 1 mm to 10 mm apart and, preferably, from 2 mm to 5 mm apart. The transverse lines of stitches may be a pattern stitch and may be crocheted or may be a basting stitch between two layers of superposed gel-forming fibers. Preferably, the lines of stitching are made in a thread such as Tencel®. The transverse stitches serve to link adjacent longitudinal lines of stitches together to add strength to the dressing in a transverse direction. The transverse lines of stitches are preferably made in columns between pairs of adjacent longitudinal lines of stitches with stitch free gaps between the columns to allow a roll of stitched gelling fabric to be slit in the gaps. This allows strips to be formed without creating loose ends of transverse stitching at the edges of the strip.

Preferably, the transverse stitching is made in a continuous zig-zag between longitudinal lines of stitching. The transverse lines of stitching can be perpendicular to the longitudinal stitching as in the case of a zig-zag castellated pattern or at an angle to it as in a continuous zig-zag angled pattern.

Preferably, the dressing comprises at least two longitudinal lines of stitching joined by a transverse line of stitching that runs in a column between the longitudinal lines. This allows the dressing to be slit from a roll with minimal loose ends of thread. More preferably, the dressing comprises at least four longitudinal lines of stitching arranged as two or more pairs of lines where the longitudinal lines of stitching in each pair are joined by a transverse line of stitching in the form of a column. This arrangement allows the user to further cut the dressing in the stitch free gap between the pairs of longitudinal lines of stitching to create a narrower ribbon.

The dressing may comprise one or more medicaments. For example, an antimicrobial agent, or an antibiotic, or an anesthetic on an anti-inflammatory agent, or a skin protective agent, or an odor absorbing agent.

Carboxymethylation can be achieved, for example, by sequential or simultaneous treatment of the cellulosic material with a strong alkali, such as aqueous sodium hydroxide, and monochloroacetic acid or a salt thereof. The appropriate reaction conditions will depend upon the composition of the fabric and the degree of carboxymethylation required and will be readily apparent to the person skilled in the art. They may be identical or similar to those described in WO 93/12275, WO 94/16746 or WO 00/01425 to which the reader is directed for further detail.

Desirably, the carboxymethylation is carried out in the presence of industrial methylated spirits (IMS), and IMS is preferably also used in a subsequent washing step, suitably along with water, as a cleaner and sterilizer. The degree of carboxymethylation is desirably such that upon absorption of exudate the fibers at the skin-contacting surface of the bandage form a gel. In a further aspect, the invention provides a method of manufacturing a wound dressing for use in cavity or sinus wounds characterized in that the method comprises the steps of:

(i) forming a roll of fabric comprising gel-forming fibers;
(ii) stitching the roll with lines of longitudinal stitching;
(iii) stitching the roll with lines of transverse stitching; and
(iv) slitting the roll in a longitudinal direction to form strips.

For example, the roll of fabric can be formed by any convenient method such as making a non-woven web of gel-forming fibers or by knitting a roll of gel-forming fibers. If desired, a non-woven web can be made by hydroentangling a web of Lyocell fibers and carboxymethylating the so-formed web.

Preferably, the transverse stitching is made in columns joining the longitudinal lines of stitching so that stitch free gaps are created between the columns. In this way a ribbon can be slit from the roll in the gaps so that minimal loose ends occur at the edges of the strip which could otherwise be lost into the wound. Preferably, the columns of transverse stitches are secured so that there are no loose threads in the gaps between the columns and the edges of the ribbon or strip have no loose ends. Preferably, the columns of transverse stitches are a continuous line of stitching which zig-zags between the longitudinal lines of stitches. In this way the columns have stitch free gaps in the space between the columns which allow the roll to be slit into strips with no loose ends at their edges. Also, the transverse lines of stitching can be finished at the longitudinal edges of the strip to reduce fraying, and can be made in columns less than the width of the roll.

Preferably, the dressing has several pairs of lines of longitudinal stitching with the lines in each pair joined by transverse stitching in a castellated pattern to create stitch free gaps between adjacent pairs of joined longitudinal lines of stitches. This allows the dressing to be cut into thinner ribbons by the user.

DETAILED DESCRIPTION OF THE PREFERRED EMBODIMENTS

Figure 1:
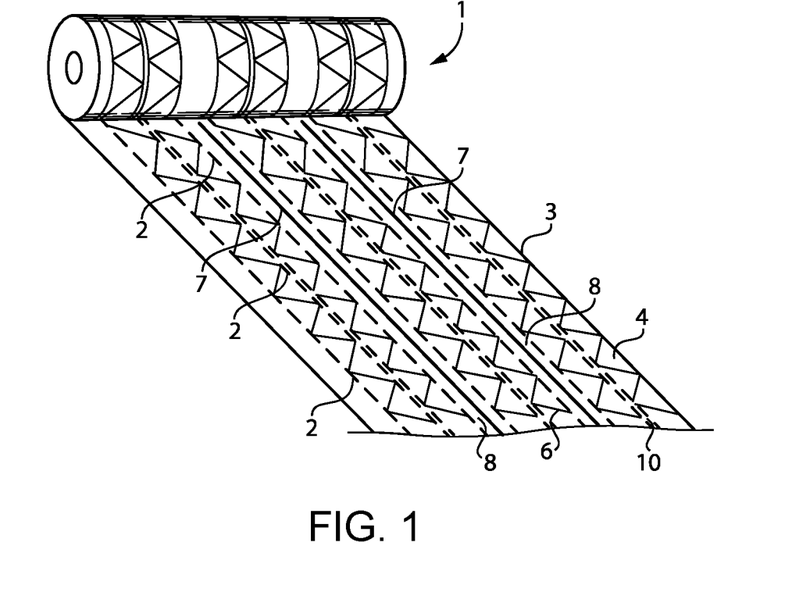
FIG. 1 is a view of a layer of gel-forming fibers in the form of a roll (1) with longitudinal lines of stitching (2) joined by transverse lines of stitching (4) in the form of an angular zig-zag (6) prior to slitting.

FIG. 1 shows a nonwoven roll (1) of gel-forming fibers made by a needle felting carding technique to form a web. Optionally, the roll (1) can have an antimicrobial material incorporated into it and, in particular, silver by the method described in WO 02/43743. The roll is stitched in the longitudinal direction with lines of stitching in Tencel® yarn. The longitudinal lines of stitches (2) are supplemented by transverse lines of stitching (4) in the form of continuous, angular zig-zags (6) which extend between adjacent longitudinal lines of stitches. In this way stitch free gaps (8) are left between columns (10) of longitudinal stitching. The roll is slit in the longitudinal direction in the stitch free gaps (8) to form ribbons. The roll (1) includes a long edge (3) and longitudinal slits (7).

Figure 2:
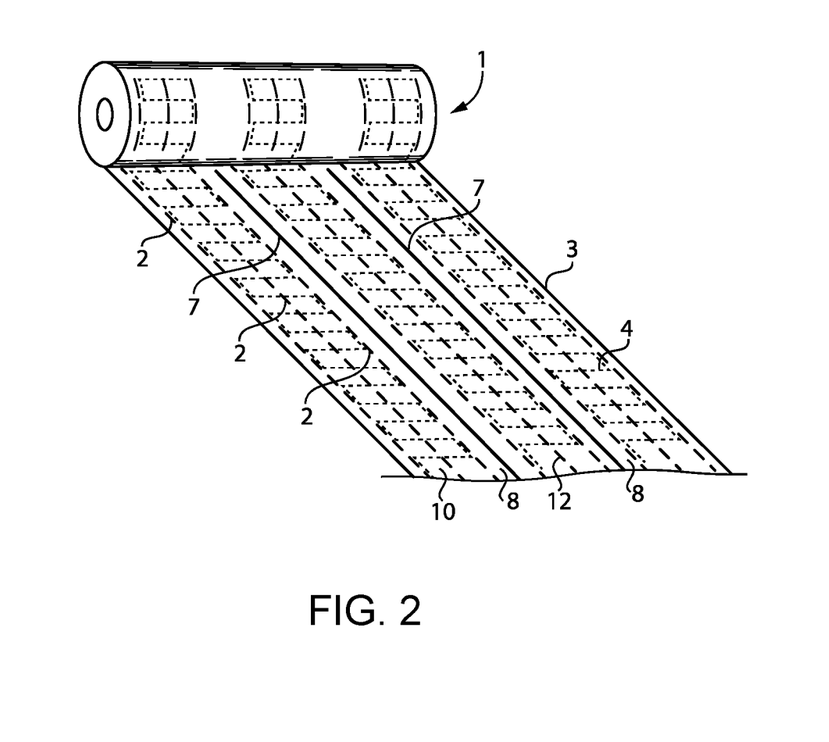
FIG. 2 is a view of a layer of gel-forming fibers in the form of a roll with longitudinal lines of stitching (2) and transverse lines of stitching (4) in the form of a castellated pattern (12) prior to slitting.
Figure 3:
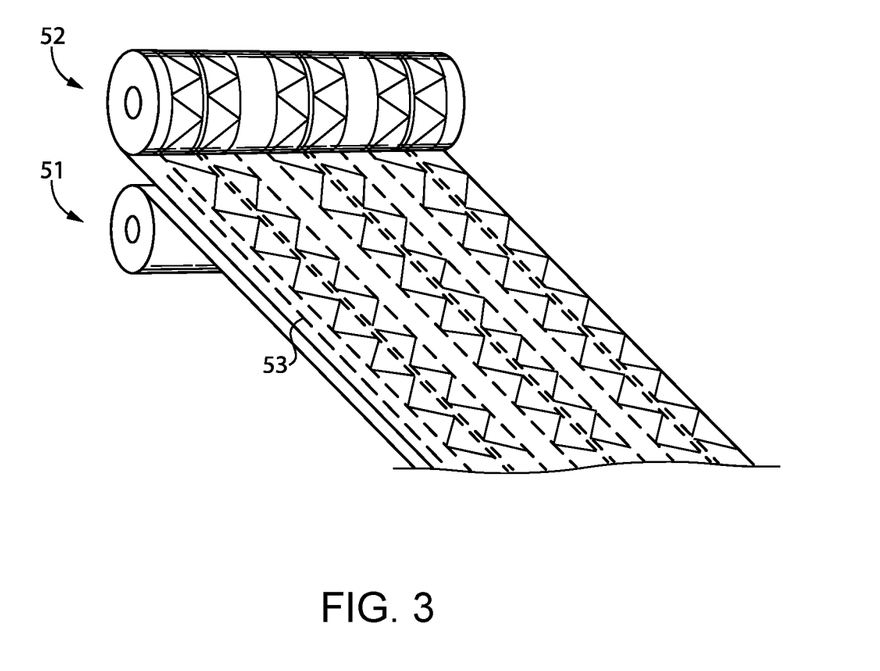
FIG. 3 illustrates a first fabric roll (51) and a second fabric roll (52) superposed on the first fabric roll (51), with the rolls (51, 52) being joined by stitching (53).

FIG. 2 shows a nonwoven roll (1) similar to that shown in FIG. 1 except that the continuous zig-zag of transverse stitches (4) is made in a castellated pattern (12) between the longitudinal lines of stitches (2) and joins them together. The roll is slit in the longitudinal direction in the stitch free gaps (8) to form ribbons. The roll (1) includes a long edge (3) and longitudinal slits (7).

Preferred embodiments of the invention will now be described with reference to the following examples:

Example 1

Dressing A

A wound dressing was made from a roll of gel-forming fibers as described for the dressing of FIG. 1. The roll had lines of longitudinal stitching spaced 5 mm apart. The column width was 2.5 cm. Ribbons were cut from each roll by slitting in a longitudinal direction at the gaps between the columns in the transverse stitching.

Dressing B

An alternative wound dressing was made by superposing two rolls of gel-forming fibers as described for Dressing A and stitching as described for Dressing A.

Dressing C

An alternative wound dressing was made by eliminating the transverse stitching of Dressing A.

Dressing D

Dressing D was formed from 100 gsm Aquacel® a nonwoven dressing made from fibers of carboxymethyl cellulose manufactured by ConvaTec Inc.

Test samples were cut from the stitched rolls to have the dimensions 25 mm wide by 100 mm long for the wet samples and 25 mm wide by 75 mm long for the dry samples. The tensile strength of the gelled and dry samples were measured in the longitudinal and transverse direction in the following manner.

Dry Tensile Testing

Samples were conditioned at 20° C.±2° C. and 65%±4% relative humidity for a minimum period of 24 hours. The samples were secured in the pneumatic jaws of a Zwicke fitted with a 100N load cell. The sample was elongated at a speed of 100 mmimin until a 75% reduction in the sample's maximum force was measured.

Wet Tensile Testing

Samples were conditioned at 20° C.±2° C. and 65%±4% relative humidity for a minimum period of 24 hours. 2 ml of a sodium and calcium chloride solution BP (British Pharmacopeia) was dispensed via a pipette onto the center of the sample and left for a period of 1 minute. The sample was secured within the pneumatic jaws of a Zwick® U.T.M. fitted with a 100N load cell. The sample was elongated at a speed of 100 mmimin until a 75% reduction in the sample's maximum force was measured.

The results are given below where MD=Machine Direction and TD=Transverse Direction.

|  | Property | | | |
| --- | --- | --- | --- | --- |
|  | Dry Tensile | | Wet Tensile | |
| Measurement | MD N/cm | TD N/cm | MD N/cm | TD N/cm |
| Dressing D | 5.33 | 16.19 | 0.16 | 0.42 |
| Dressing B | 8.04 | 20.82 | 4.51 | 4.39 |
| Dressing C | 13.51 | 15.75 | 8.00 | 0.44 |
| Dressing A | 12.19 | 30.78 | 8.05 | 4.45 |

These results show the improvement in tensile strength in transverse stitched samples.

Example 2

Dressing A was used to pack a tracking wound. On removal from the wound the ribbon dressing was fully hydrated with wound fluid yet had maintained its structure. The dressing was easily removed from the wound in one piece.

The invention claimed is:

1. A wound dressing having a non-woven web of gel-forming fibers, the wound dressing comprising:
   longitudinal lines of stitches formed from thread;
   transverse lines of stitches formed from thread extending between at least two of the longitudinal lines of stitches to form a stitched column; and
   at least one stitch free column;
   wherein at least two stitched columns are formed and separated by the at least one stitch free column;
   wherein two of the transverse lines of stitches are offset from one another in a longitudinal direction by an offset distance; and
   wherein a longitudinal length of the at least one stitch free column is greater than the offset distance.

2. The wound dressing as claimed in claim 1, wherein the longitudinal lines of stitches are from 1 mm to 10 mm apart and are parallel to a long edge of the wound dressing.

3. The wound dressing as claimed in claim 1, wherein the transverse lines of stitches are stitched through the wound dressing.

4. The wound dressing as claimed in claim 1, wherein the gel-forming fibers comprise one or more of cellulose fibers, chemically modified cellulosic fibers, pectin fibers, alginate fibers, chitosan fibers, hyaluronic acid fibers, polysaccharide fibers and fibers derived from gums.

5. The wound dressing as claimed in claim 1, wherein the thread comprises one or more of nylon, polyolefin, polyurethane, polyester, cellulosic, and modified cellulosic.

6. The wound dressing as claimed in claim 1, wherein the transverse lines of stitches are in the form of a continuous zig-zag.

7. The wound dressing as claimed in claim 1, wherein the wound dressing has a slit in a longitudinal direction in the at least one stitch free column, and wherein the slit is configured to remove any loose thread from the transverse lines of stitches at longitudinal edges.

8. The wound dressing as claimed in claim 1, wherein the transverse lines of stitches are in the form of a castellated pattern.

9. The wound dressing as claimed in claim 1, wherein the wound dressing forms a strip.

10. A method of manufacturing a wound dressing, the method comprising:
    forming a first roll of fabric comprising a non woven web of gel-forming fibers;
    forming a first stitched column formed by longitudinal lines of stitches having transverse lines of stitching formed from thread extending between the longitudinal lines of stitches, wherein two of the transverse lines of stitching are offset from one another in a longitudinal direction by an offset distance; and
    forming a second stitched column spaced from the first stitched column to create a stitch-free column between the first stitched column and the second stitched column;
    wherein a longitudinal length of the stitch-free column is greater than the offset distance.

11. The method as claimed in claim 10, wherein the first roll of fabric is formed by knitting a roll of gel-forming fibers.

12. The method as claimed in claim 10, wherein the nonwoven web is made by hydroentangling a web of lyocell fibers and carboxymethylating the web.

13. The method as claimed in claim 10, wherein the method comprises the further step of treating the dressing with a source of silver.

14. The method as claimed in claim 10, wherein the dressing has no loose thread from the transverse lines of stitching at longitudinal edges.

15. The method as claimed in claim 10, further comprising superposing a second roll of fabric comprising a non woven web of gel-forming fibers on the first roll of fabric and stitching the first and second roll together.

16. A wound dressing, comprising:
    a non woven web of gel-forming fibers;
    transverse lines of stitches extending between longitudinal lines of stitches to form columns;
    wherein the transverse lines of stitches are finished at an edge of at least two longitudinal lines of stitches, and wherein the transverse lines of stitches are stitched through the wound dressing.

17. The wound dressing as claimed in claim 16, wherein the gel-forming fibers comprise one or more of spun cellulose fibers, chemically modified cellulosic fibers, pectin fibers, alginate fibers, chitosan fibers, hyaluronic acid fibers, other polysaccharide fibers and fibers derived from gums.

18. The wound dressing as claimed in claim 16, wherein the stitches are formed of thread, and wherein the thread comprises one or more of nylon, polyolefin, polyurethane, polyester, cellulosic, or modified cellulosic.

* * * * *